United States Patent
Schmitt

(10) Patent No.: US 8,000,770 B2
(45) Date of Patent: Aug. 16, 2011

(54) MAGNETIC RESONANCE APPARATUS WITH TABLE MOVEMENT CONTROLLED DEPENDENT ON MAGNETIC FIELD DISTRIBUTION

(75) Inventor: Franz Schmitt, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1009 days.

(21) Appl. No.: 11/777,334

(22) Filed: Jul. 13, 2007

(65) Prior Publication Data

US 2008/0015431 A1 Jan. 17, 2008

(30) Foreign Application Priority Data

Jul. 14, 2006 (DE) .......................... 10 2006 032 798

(51) Int. Cl.
*A61B 5/055* (2006.01)
(52) U.S. Cl. ........................................ 600/415; 324/309
(58) Field of Classification Search .................. 600/415; 324/309
See application file for complete search history.

(56) References Cited

U.S. PATENT DOCUMENTS

| 6,230,040 | B1 * | 5/2001 | Wang et al. | 600/415 |
| 6,269,501 | B1 * | 8/2001 | Li et al. | 5/601 |
| 6,759,847 | B2 | 7/2004 | Brinker et al. | |
| 2004/0147835 | A1 * | 7/2004 | Kiefer et al. | 600/410 |

OTHER PUBLICATIONS

"Calculation of Electric Fields Induced by Body and Head Motion in High-Field MRI," Liu et al., Journal of Magnetic Resonance, vol. 161 (2003) pp. 99-107.

* cited by examiner

*Primary Examiner* — Brian Casler
*Assistant Examiner* — Jonathan G Cwern
(74) *Attorney, Agent, or Firm* — Schiff Hardin LLP

(57) ABSTRACT

A magnetic resonance device has a patient bed able to be automatically moved by means of a drive apparatus into a patient chamber, as well as a magnet arrangement for creating a magnetic field in the interior of the patient chamber. The drive apparatus is operated so as to move the patient bed at a speed determined as a function of the distribution of the magnetic field in the direction of movement of the patient bed.

13 Claims, 3 Drawing Sheets

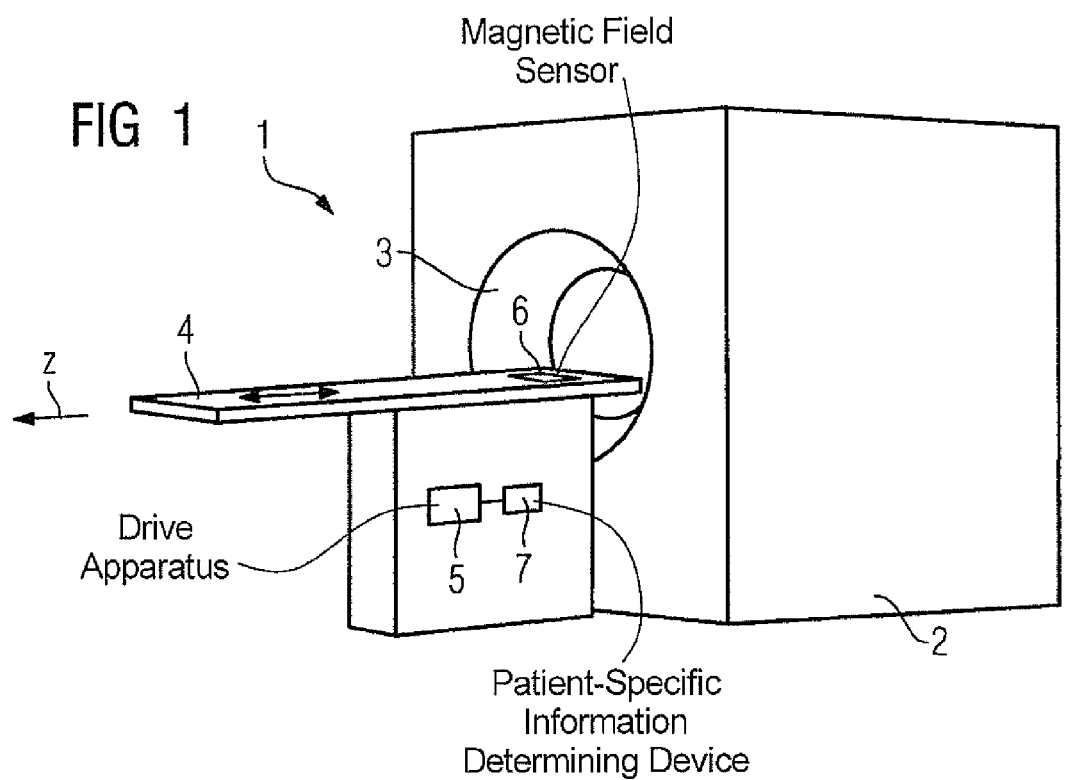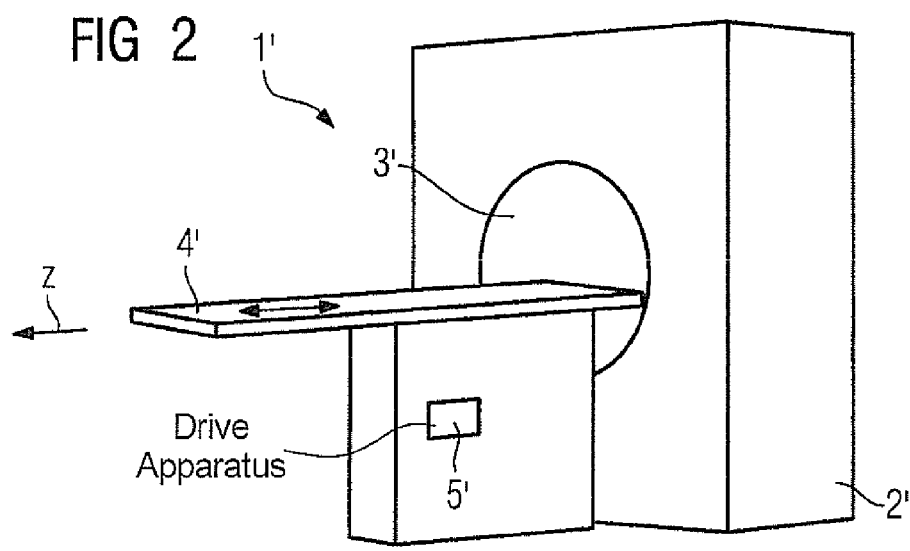

MAGNETIC RESONANCE APPARATUS WITH TABLE MOVEMENT CONTROLLED DEPENDENT ON MAGNETIC FIELD DISTRIBUTION

BACKGROUND OF THE INVENTION

1. Field of the Invention

The invention relates to a magnetic resonance device of the type having a patient bed able to be moved into a patient chamber automatically by means of a drive apparatus, as well as a magnet arrangement for creating a magnetic field within the patient chamber.

2. Description of the Prior Art

Magnetic resonance devices of the above type for obtaining magnetic resonance images are widely known. Since the patient chamber frequently has quite a small diameter, the patient is placed on the patient bed outside the patient chamber, after which the patient bed can be automatically moved into the patient chamber by means of the drive apparatus.

With the advent of high-field magnetic resonance devices, for example with fields of up to 7T, patients have been reporting side-effects when they are introduced into the patient chamber. These side effects manifest themselves, for example, in the form of a feeling of dizziness or a metallic taste. These side effects can be correlated with the speed of the patient bed upon entry into or exit from the patient chamber, with more side-effects occurring at higher speeds. If such high-field magnetic resonance devices are to employed on a regular basis in clinical practice, this is a disadvantage that needs to be rectified.

SUMMARY OF THE INVENTION

An object of the present invention is therefore to provide a magnetic resonance device in which side-effects occurring on entry or exit of the patient bed into or from the patient chamber are minimized.

This object is achieved in accordance with the invention by a magnetic resonance device of the type initially described, wherein the drive apparatus is operated so as to move the patient bed at a specific speed determined as a function of the field distribution of the magnetic field in the direction of movement of the patient bed.

The reasons underlying the adverse comments made by patients have been recognized within the context of the present invention. If the direction of movement of the patient bed along the z direction (as is typical) occurs, the magnetic field $B_z$ will increase on entry into the patient chamber as the movement distance increases, on exit it will decrease as the movement distance increases. The magnetic field is consequently not constant along the movement path, but a field distribution exists, so that changes in the magnetic field occur along the movement path. Since human beings are by and large diamagnetic, a location-dependent diamagnetic force is generated on the human body by this field distribution, which triggers the uncomfortable feelings in the patient. It has been shown in investigations that it is precisely in the area in which strong changes occur in the field distribution that the side effects have been observed in test subjects.

In accordance with the invention, the drive apparatus is operated to move the patient bed at a specific speed that is determined as a function of the field distribution of the magnetic field in the direction of movement of the patient bed. This means that knowledge about the field distribution along the movement path is advantageously used to select a constant speed at which the side-effects are minimized, or to control the speed in a location-dependent way. The detection of the field distribution along the movement path can be undertaken in a one-time calibration measurement, or alternatively a magnetic field sensor can be provided on the patient bed itself, so that the current field distribution is always determined. A convenient introduction and removal of the patient without any side-effects on the patient is achieved in this way.

In a first embodiment of the present invention the drive apparatus can be embodied for moving the patient bed at a constant speed determined on the basis of a maximum force exerted on the patient as a result of the field distribution. This means that the point at which the strongest changes in the field distribution of the magnetic field occur is determined, from which, in conjunction with the magnetic field itself a diamagnetic force is produced. This force furthermore also depends on the speed of the patient bed, i.e. of the patient. With a lower speed a lower force is obtained. The speed of the patient bed is now adjusted so that it is moved at a constant speed at which with the greatest possible force as well as no perceptible side-effects occur.

As an alternative or in addition, the drive apparatus can be controlled as to its the location-dependent speed on the basis of a control value describing the field distribution at the current location of the patient bed. In the previously mentioned case of the constant speed, this will be very slow overall, so that the introduction or removal of the patient into or from the patient chamber proceeds rather slowly. If this process is advantageously to be accelerated, a location-dependent control of the speed on the basis of a control value can be provided, so that the patient bed moves more slowly in areas in which a large diamagnetic force is to be expected, and otherwise an appropriately rapid speed of movement is used.

In this case two options are again possible, which have already been addressed above. The field distribution or the control value can be measured or determined beforehand, so that a characteristic curve is now available that specifies the control value—or directly the speed derived from it—as a function of the location. On the basis of this characteristic curve or with further control parameters of this characteristic curve family, the speed of the patient bed is controlled by the drive apparatus.

Alternatively it is of course also possible for the control value to be determined using a detection result of at least one suitable detector at the current point in time in each case. In this case the magnetic resonance system can include a detector communicating with the drive apparatus for detecting the field distribution, with the control value being determined on the basis of the detection result. Such a detector can be a magnetic field sensor, or it can be a force sensor, for example, which directly measures the diamagnetic force. If a magnetic field sensor is provided, the gradient of the magnetic field and also the shape of the diamagnetic force curve can be determined from consecutive measured values. This control value can then be used directly as an input variable for control.

Expediently the position of the detector can be selected so that, for a patient lying on a patient bed, it expresses a specific electrophysiological location of this patient. Accordingly, the detector can be arranged at a position corresponding to an electrophysiological location of a patient located on the patient bed, especially at the height of the head or of the heart. Feelings of dizziness occur in the patient's head, so that to avoid such feelings it is useful to determine the field distribution in relation to this location. Another possible location is a position corresponding to the heart of the patient, since the largest amount of moving blood, which also includes moving charge carriers, is located in the aortic arch. The detector is then ideally arranged on or in the patient bed at the corresponding location and communicates with the drive apparatus, with the detection result of the detector either already being evaluated by the detector itself for determining the control value, or the control value being determined in the drive apparatus using to the detection result. It is also possible to provide two or more detector, with for example one being arranged at the head and another at the heart.

In an embodiment the control value can be the gradient of the magnetic field in the direction of movement. The gradient of the magnetic field specifies the strength of the change in the field distribution. This is also directly included in the resulting diamagnetic force, so that the gradient is a meaningful control value.

Alternatively the control value can be the product of the magnetic field with the gradient of the magnetic field in the direction of movement. The diamagnetic force is proportional to the product just indicated, so that the curve of the diamagnetic force defined by the field distribution along the direction of movement is in the final analysis included directly here as the control value. This means that an ideal synchronization is possible.

As already mentioned, the diamagnetic force created as a result of the field distribution also increases linearly with the speed of the patient bed, and thus the speed of movement of the patient. Accordingly, it is advantageous for the speed to be able to be controlled linearly with the inverse of the control value. In the case of the product of magnetic field and gradients of the magnetic field, the influence of the distribution on the diamagnetic force arising is just equalized, so that it can be advantageously achieved that, along the movement path, essentially the same completely harmless force acts on the patient.

This aforementioned maximum force is predetermined by further parameters that are defined, for example, with reference to comfort criteria. In the final analysis the force is determined so that possible side-effects can no longer occur.

A "pure" control on the basis of the inverse of the control value could, however, lead to very high speeds, which in turn could be unpleasant for the patient. Provision thus can be made for the drive apparatus to take account of a maximum speed that regardless of the control value, cannot be exceeded. With very small changes in the magnetic field distribution the speed is thus not increased without limit, but at most up to the predetermined maximum speed. In this way a comfortable movement of the patient over the entire movement path can be ensured.

Similarly, the drive apparatus can take account of a minimum speed which cannot be undershot regardless of the control value. This is meaningful because the speed, as a result of a greatly variable magnetic field in the direction of movement, may become so low that it is once again uncomfortable to introduce the patient extremely slowly into the patient chamber or to remove the patient from it again.

For a speed regulation that provides particular comfort, individual characteristics of the patient can additionally be taken into consideration. To this end the drive apparatus can be control the speed as a function of at least one item of patient-specific information. Such patient-specific information can be, for example, the weight and/or the age of the patient. In the case of controlling the location-dependent speed on the basis of the control value not just one characteristic curve can then be provided, but a characteristic curve family for different ages or weight groups. An especially pleasant transport of the patient into and out of the patient chamber is then advantageously possible, which additionally takes account of the physical state of the patient.

Expediently a device can be provided in this case for determination of the patient-specific information. Thus it is possible for scales to be integrated into the patient bed, with which the weight of the patient can be determined and transmitted to the drive apparatus. As an alternative or in addition, a communication device can be provided that communicates, for example, with a server with patient files, from which relevant patient-specific information, for example the age of the patient or the physical state of the patient, especially how much stress the patient can withstand, can be requested. The communication device, which can also be integrated into the drive apparatus, then transmits the corresponding patient-specific information to the drive apparatus. It is also possible for an input device to be provided, by means of which the patient-specific information is able to be input.

The inventive magnetic resonance device can be a whole-body magnetic resonance device, in which the patient is completely enclosed by the patient chamber, so that areas of the whole body can be imaged, or can be a so-called head magnetic resonance device, which is designed specifically for recording images of the head. In this case only the head and where necessary a part of the upper body of the patient is moved into the patient chamber. Stronger side-effects have been observed previously with such head magnetic resonance devices, which can be minimized with the aid of the present invention.

BRIEF DESCRIPTION OF THE DRAWINGS

FIG. 1 schematically illustrates a whole-body magnetic resonance device in accordance with the invention.

FIG. 2 schematically illustrates a head magnetic resonance device in accordance with the invention.

DESCRIPTION OF THE PREFERRED EMBODIMENTS

Figure 3:
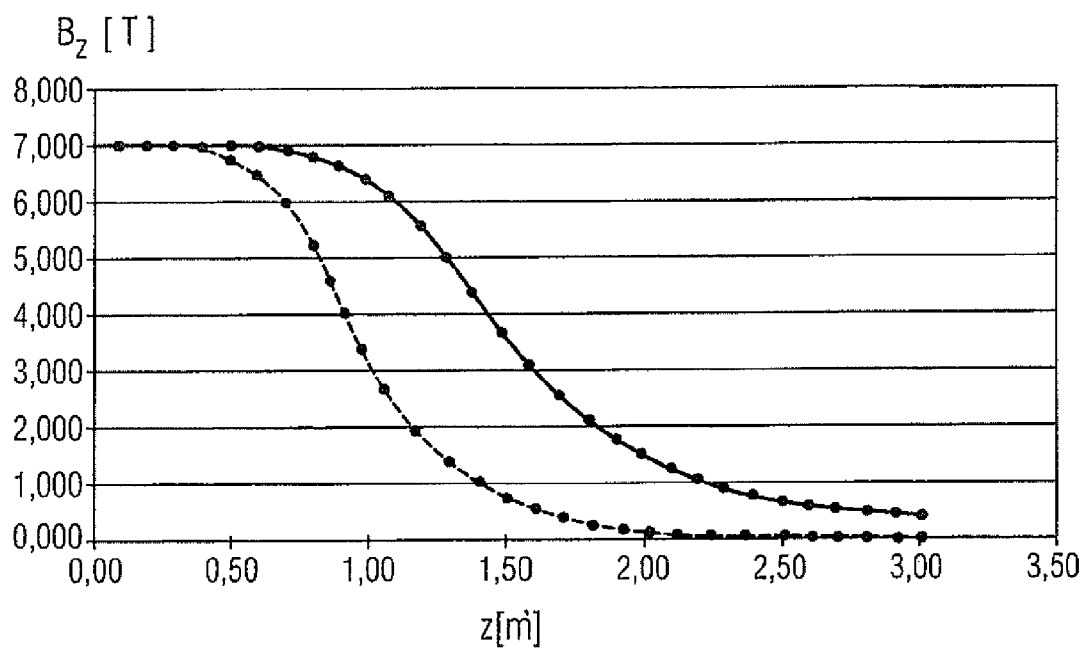
FIG. 3 is a graph in which the magnetic field is plotted in the direction of movement against the location.

FIG. 1 shows an inventive magnetic resonance device 1 which is embodied as a whole-body magnetic resonance device. The device 1 includes a magnet arrangement 2, not shown in greater detail, which creates a magnetic field within a patient chamber 3. By means of a patient bed 4 movable along the z-direction, i.e. the direction of movement of the magnetic resonance device 1 a patient can be introduced into the patient chamber 3 and removed from it once again. The patient bed 4 is able to be moved automatically via a drive apparatus 5 which also determines the speed of the patient bed 4.

In this case the drive apparatus 5 is embodied to move the patient bed 4 at a speed determined as a function of the field distribution of the magnetic field in the direction of movement of the patient bed. In addition to conventional mechanical components, the drive apparatus 5 includes one or more control components that operate the mechanical components in accordance with the invention. At least two operating options are possible in this exemplary embodiment, which can be available at the same time, or a switchover between these operating modes can be undertaken, for example by means of an input device operable by a user.

The drive apparatus 5 can move the patient bed 4 at a constant, speed determined on the basis of a maximum force exerted as a result of the field distribution on the patient. As an alternative or in addition the drive apparatus 5 can control the location-dependent speed based on a control value describing the field distribution at the current location of patient bed 4.

It is therefore necessary in the two operating modes to know the field distribution along the movement path in the z direction. A magnetic field sensor 6 which is moved with the patient bed 4 is provided to detect this field distribution. This does not have to be constantly present in the magnetic resonance device 1, it is also conceivable to fit it for one-off recording of a field distribution to the patient bed 4 and to determine from the field distribution determined the constant speed or to create one of more characteristic curves for controlling the speed as a function of the location. In any event the regulation of the speed can also be determined on the basis of current measurement data, of the magnetic field sensor 6 for example.

It can be seen that the magnetic field sensor 6 is arranged at the height of the head of the patient located on the patient bed 4. This means that the magnetic field is measured directly at the location at which the relevant side-effects, here the feeling of dizziness, also arise. As an alternative or in addition it would also be possible to fit the magnetic field sensor or a further sensor 6 at a position corresponding to the location of the patient's heart on the patient bed 4.

If the control value is determined as a function of the detection result of the magnetic field sensor 6 a communication link exists between the magnetic field sensor 6 and the drive apparatus 5. If the detection result is not directly used for control, the control value can be determined from the detection results either by the magnetic field sensor 6 or by the drive apparatus 5.

A characteristic curve field or a number of speeds are then required, if further parameters are included in the final determination of the speed by the drive apparatus 5. Such parameters can for example be individual, patient-specific information. Thus a device 7 for determining the patient-specific information is also provided for the magnetic resonance device 1. This is embodied here as a communication device which communicates with the drive apparatus 5 and can interrogate data of a patient file stored on an external server. Suitable patient-specific information is for example the age of the patient, or the patient's physical ability to withstand stress, or the patient's weight. To this end the device 7 can also be a set of scales for example.

FIG. 2 shows an alternate embodiment of a magnetic resonance device 1', which is embodied here as a head magnetic resonance device. The magnet arrangement 2' and the patient opening 3' are visibly embodied shorter and somewhat narrower, so that the device 1' is optimally designed for recording images of the head. Likewise a patient bed 4' is provided which is moved by a drive apparatus 5'. The functioning of the individual components is precisely as already described in relation to the magnetic resonance device 1.

FIG. 3 shows a graph in which the z component $B_z$ of the magnetic field, which is created by the magnetic field arrangement 2 or 2', is plotted on the ordinate, and the location z is plotted on the abscissa. It can be seen that a 7T magnet is used for magnetic resonance device 1 or 1', respectively. The location 0 on the z axis has been placed here at the isocenter of the magnet arrangement 2 of 2', respectively, which is located in the interior of the patient chamber 3 or 3' respectively. The solid-line curve corresponds in this case to the field distribution in magnetic resonance device 1 (whole-body magnetic resonance device), the dashed-line curve to the field distribution in magnetic resonance device 1' (head magnetic resonance device). It can be seen that the magnetic field initially remains essentially homogeneous within the patient chamber 3, i.e. at a constant value of 7T. On exit from the support 3, however, a drop is to be expected, which is sharper for the head magnetic resonance device 1'. This is to be seen as correlating with examinations in which patients in a head magnetic resonance device have complained of greater side-effects than in a whole-body magnetic resonance device.

Figure 4:
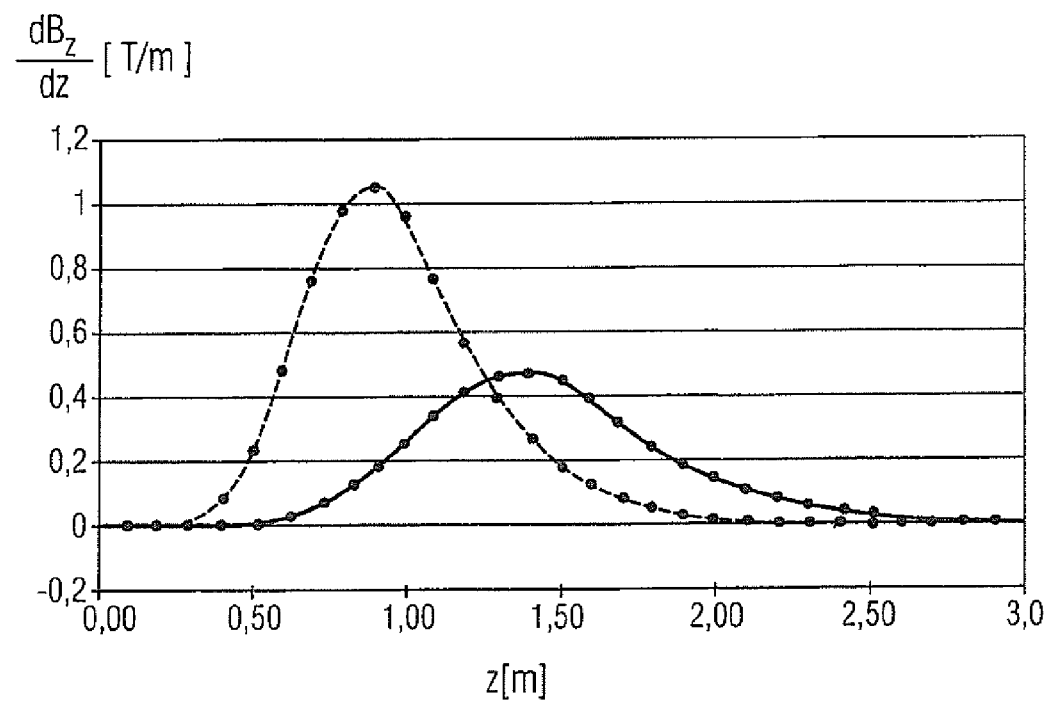
FIG. 4 is a graph in which the gradient of the magnetic field in the direction of movement is plotted against the location.

FIG. 4 shows the gradient 5 $dB_z/dz$ of the magnetic field $B_z$ in the z direction, i.e. the direction of movement of the patient bed 4 or 4' respectively, plotted against the location z. Once more the solid-line curve shows the gradient for the magnetic resonance device 1, the dashed-line curve the gradient for the magnetic resonance device 1'. The gradient is at its highest when the field distribution changes most strongly, with higher values being reached for the head magnetic resonance device 1'.

Figure 5:
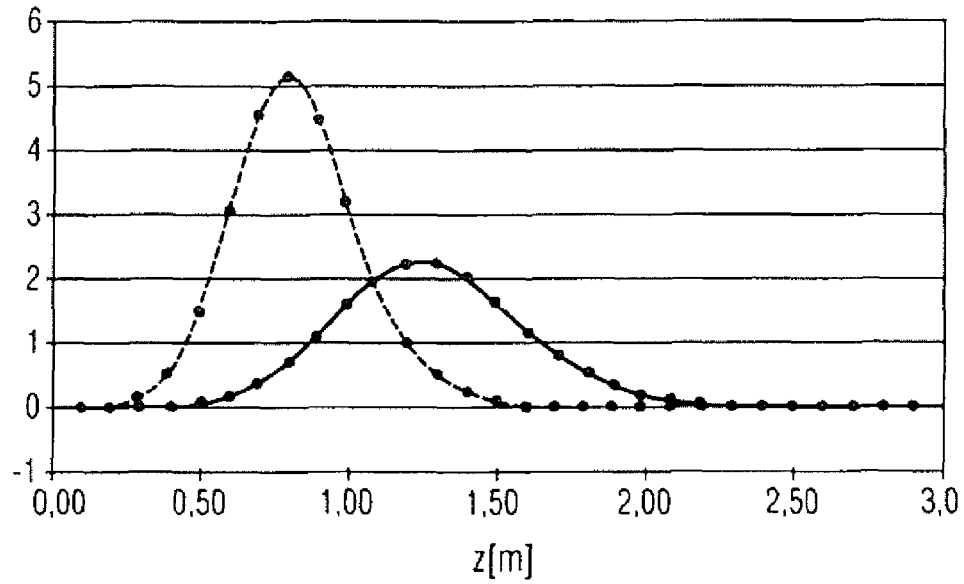
FIG. 5 is a graph in which the product of the magnetic field with the gradient of the magnetic field is plotted against the location.

The diamagnetic force, which is exerted on a diamagnetic body, is proportional to the product A of the magnetic field $B_z$ with the gradient of the magnetic field 5 $dB_z/dz$. This product consequently reflects the diamagnetic force as a function of the field distribution. This is shown in FIG. 5 on the ordinate as a function of the location z plotted on the abscissa. Once again the solid-line curve represents the product for the magnetic resonance device 1, the dashed-line curve the product for the magnetic resonance device 1'. It can be seen that greater forces occur in the head magnetic resonance device 1'.

The drive apparatus 5 or 5' respectively is now embodied to determine the speed of the patient bed 4 or 4' respectively as a function of the field distribution shown. If one also defines $$A = B_z(z) \cdot \frac{dB_z}{dz}(z), \quad (1)$$

the drive apparatus 5 or 5' respectively determines, for control of the location-dependent speed the speed of the patient bed 4 or 4' respectively in the exemplary embodiment on the basis of the formula $$v(z) = v_0 + \frac{c}{A}. \quad (2)$$

The speed is thus a linear function of the inverse of the product A, but at the same time it is also true that the force is a linear function of the speed. This means that the effect of the force on the speed is simply cancelled out in the final analysis. The parameters $V_0$ and c are in this case to be determined empirically.

Since the product A, as can be seen from FIG. 5, can be very small, this means however that very high speeds can result for the formula (2) specified above. Since this is not in the interest of patient comfort, the drive apparatus 5 or 5' respectively is also to take account of the maximum speed $v_{max}$ which cannot be exceeded regardless of the control value.

Figure 6:
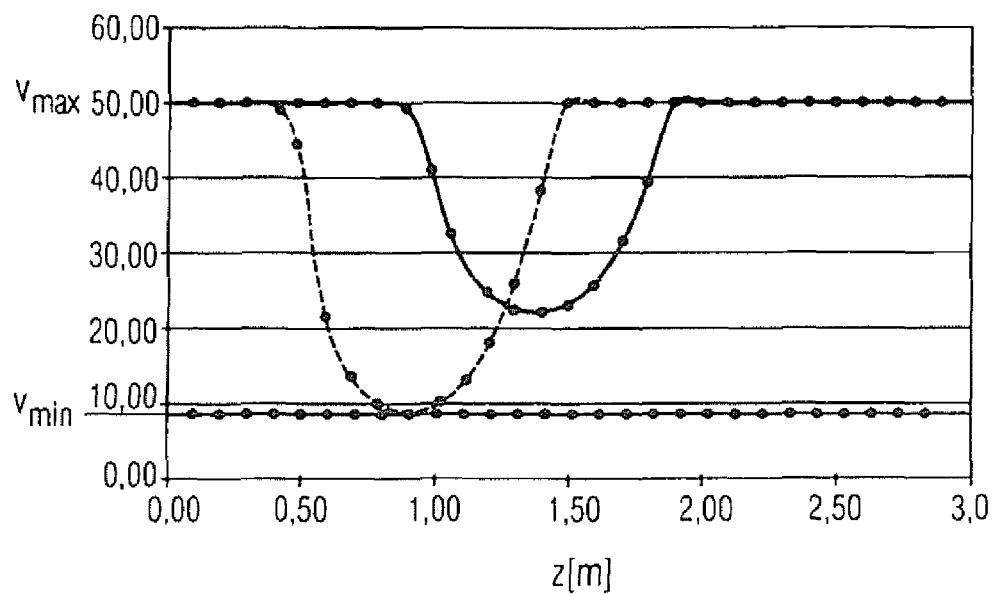
FIG. 6 is a graph in which the speed of the patient bed is plotted against the location.

The speed curve produced is shown in FIG. 6. In this figure the solid line again indicates the speed produced in the case of the magnetic resonance device 1, the dashed line indicates the speed produced in the case of the magnetic resonance device 1'. The speed is plotted here in any given units. It can be seen that the maximum speed $v_{max}$, which amounts to 50 in the example, is not exceeded. In the areas in which the speed determined with the above formula (2) thus produces a higher value than $v_{max}$, the patient bed 4 or 4' respectively is moved at the maximum speed $v_{max}$. If however a strong change in the field distribution is noticed, cf. FIG. 5, the speeds determined with formula (2) are lower than as $v_{max}$, so that now, to avoid side-effects, these speeds are taken into account, meaning that the patient bed 4 or 4' respectively is moved at a slower speed. In this case lower speeds are necessary for the head magnetic resonance device 1' since the force exerted is greater.

As explained above, it is alternatively possible for the drive apparatus 5 or 5', respectively for driving the patient bed 4 or 4', respectively, to be embodied with constant speed. This constant speed is then determined from the minimum of the curves shown in FIG. 6 which is shown for example for the dashed curve for the magnetic resonance device 1' as $v_{min}$.

If additional parameters are included in the speed control, for example the patient-specific information already mentioned, a set of characteristic curves of a set of constant speeds is provided.

Although modifications and changes may be suggested by those skilled in the art, it is the intention of the inventors to embody within the patent warranted hereon all changes and modifications as reasonably and properly come within the scope of their contribution to the art.

I claim as my invention:

1. A magnetic resonance device comprising:
   a magnetic resonance scanner having a patient chamber configured to interact with a patient and a magnet system that generates a magnetic field in an interior of said patient chamber, said magnetic field having a field distribution;
   a patient bed configured to receive a patient thereon; and
   a drive apparatus comprising a movement mechanism in driving connection with said patient bed to move said patient bed into and out of said patient chamber, and a control unit that operates said movement mechanism to move said patient bed at a nonzero speed that is a function of the field distribution of said magnetic field in a direction of movement of the patient bed.

2. A magnetic resonance device as claimed in claim 1 wherein the patient experiences a maximum force exerted on the patient as a result of said field distribution, and wherein said control unit operates said movement mechanism at a constant speed that is dependent on said maximum force.

3. A magnetic resonance device as claimed in claim 1 wherein said control unit operates said movement mechanism so that said speed of movement is location-dependent relative to a current location of the patient bed with respect to a control value representing said field distribution.

4. A magnetic resonance device as claimed in claim 3 comprising a detector in communication with said control unit that detects said field distribution and generates a detector output corresponding thereto, and wherein said control unit determines said control value from said detector output, said detector being selected from the group consisting of magnetic field sensors and force sensors.

5. A magnetic resonance device as claimed in claim 4, wherein said detector is located at a predetermined location with respect to a patient on the patient bed, selected from the group consisting of at an expected height of the head of a patient or at an expected location of the heart of a patient.

6. A magnetic resonance device as claimed in claim 3 wherein said control unit determines the gradient of the magnetic field in said direction of movement as said control value.

7. A magnetic resonance device as claimed in claim 3 wherein said control unit determines a product of a strength of the magnetic field with the gradient of the magnetic field in the direction of movement, as said control value.

8. A magnetic resonance device as claimed in claim 3 wherein said control unit controls said speed of said patient bed linearly dependent on the inverse of said control value.

9. A magnetic resonance device as claimed in claim 3 wherein said control unit limits movement of said patient bed to a maximum speed that cannot be exceeded regardless of said control value.

10. A magnetic resonance device as claimed in claim 3 wherein said control unit limits said speed of said patient bed to a minimum value that must be maintained regardless of said control value.

11. A magnetic resonance device as claimed in claim 1 wherein said control unit controls said speed of said patient bed as a function of at least one item of patient-specific information associated with the patient.

12. A magnetic resonance device as claimed in claim 11 comprising a patient information identifying device disposed in said magnetic resonance scanner and configured to interact with the patient on the patient bed to obtain said at least one item of patient-specific information.

13. A magnetic resonance device as claimed in claim 11 comprising a data bank containing said patient-specific information, said data bank being accessible by said control unit to obtain said at least one item of patient-specific information therefrom.

* * * * *